United States Patent [19]
Gould et al.

[11] Patent Number: 4,543,435
[45] Date of Patent: Sep. 24, 1985

[54] MULTISTAGE PROCESS FOR CONVERTING OXYGENATES TO LIQUID HYDROCARBONS WITH ETHENE RECYCLE

[75] Inventors: Ronald M. Gould, Sewell; Samuel A. Tabak, Wenonah, both of N.J.

[73] Assignee: Mobil Oil Corporation, New York, N.Y.

[21] Appl. No.: 692,261

[22] Filed: Jan. 17, 1985

[51] Int. Cl.[4] .............................................. C07C 5/00
[52] U.S. Cl. .................................... 585/330; 422/188; 585/312; 585/314; 585/315; 585/316; 585/324; 585/327; 585/640; 585/469; 585/733
[58] Field of Search ............... 585/330, 324, 312, 314, 585/315, 316, 329, 640, 469, 733, 7 SM; 422/188

[56] References Cited
U.S. PATENT DOCUMENTS

| | | | |
|---|---|---|---|
| 3,928,483 | 12/1975 | Chang et al. | 260/668 |
| 3,965,205 | 6/1976 | Garwood et al. | 260/668 |
| 4,025,576 | 5/1977 | Chang et al. | 260/682 |
| 4,058,576 | 11/1977 | Chang et al. | 260/673 |
| 4,433,185 | 2/1984 | Tabak | 585/312 |
| 4,450,311 | 5/1984 | Wright et al. | 585/413 |
| 4,456,779 | 6/1984 | Owen et al. | 585/415 |
| 4,482,772 | 11/1984 | Tabak | 585/254 |
| 4,497,968 | 2/1985 | Wright et al. | 585/304 |

OTHER PUBLICATIONS

"Production of Chemicals from Methanol", Warren W. Kaeding and Stephen A. Butter Journal of Catalysis, vol. 61, No. 1, Jan. 1980.
"Conversion of Methanol to Hydrocarbons", Margaret M. Wu and Warren W. Kaeding, Journal of Catalysis 88, 478–489, (1984).

Primary Examiner—D. E. Gantz
Assistant Examiner—A. Pal
Attorney, Agent, or Firm—A. J. McKillop; M. G. Gilman; L. G. Wise

[57] ABSTRACT

A process for converting oxygenated feedstock comprising methanol, dimethyl ether or the like to liquid hydrocarbons comprising the steps of contacting the feedstock with zeolite catalyst in a primary catalyst stage at elevated temperature and moderate pressure to convert feedstock to hydrocarbons comprising $C_2$–$C_4$ olefins and $C_5$+ hydrocarbons;

cooling and separating effluent from the primary stage to recover a liquid hydrocarbon stream and a light hydrocarbon vapor stream rich in $C_2$–$C_4$ olefins;

compressing the olefinic light hydrocarbon stream to condense a liquid olefinic hydrocarbon stream rich in $C_3$+ olefins and recovering an ethene-rich gaseous stream;

further pressurizing and contacting the condensed liquid olefinic hydrocarbon stream in a secondary catalytic stage with oligomerization catalyst comprising medium-pore shape selective acidic zeolite at substantially increased pressure and moderate temperature to convert at least a portion of olefins to a heavier liquid hydrocarbon product stream comprising olefinic gasoline and distillate range liquids; and recovering ethene in a gaseous stream for recycle to the primary catalytic stage.

20 Claims, 4 Drawing Figures

4,543,435

MULTISTAGE PROCESS FOR CONVERTING OXYGENATES TO LIQUID HYDROCARBONS WITH ETHENE RECYCLE

BACKGROUND OF THE INVENTION

This invention relates to an integrated system for converting oxygenates, such as methanol or dimethyl ether (DME), to liquid hydrocarbons. In particular it provides a continuous process for producing hydrocarbon products by converting the oxygenate feedstock catalytically to an intermediate lower olefinic stream and oligomerizing the olefins to produce distillate and gasoline.

In order to provide an adequate supply of liquid hydrocarbons for use as synfuels or chemical feedstocks, various processes have been developed for converting coal and natural gas to gasoline, distillate and lubricants. A substantial body of technology has grown to provide oxygenated intermediates, especially methanol. Large scale plants can convert methanol or similar aliphatic oxygenates to liquid fuels, especially gasoline. However, the demand for heavier hydrocarbons has led to the development of processes for making diesel fuel by a multi-stage technique.

Recent developments in zeolite catalysts and hydrocarbon conversion processes have created interest in utilizing olefinic feedstocks, for producing $C_5^+$ gasoline, diesel fuel, etc. In addition to the basic work derived from ZSM-5 type zeolite catalysts, a number of discoveries have contributed to the development of a new industrial process, known as Mobil Olefins to Gasoline/Distillate ("MOGD"). This process has significance as a safe, environmentally acceptable technique for utilizing feedstocks that contain lower olefins, especially $C_2$–$C_5$ alkenes. This process may supplant conventional alkylation units. In U.S. Pat. Nos. 3,960,978 and 4,021,502, Plank, Rosinski and Givens disclose conversion of $C_2$–$C_5$ olefins, alone or in admixture with paraffinic components, into higher hydrocarbons over crystalline zeolites having controlled acidity. Garwood et al have also contributed improved processing techniques to the MOGD system, as in U.S. Pat. Nos. 4,150,062, 4,211,640 and 4,227,992. The above-identified disclosures are incorporated herein by reference.

Conversion of lower olefins, especially propene and butenes, over HZSM-5 is effective at moderately elevated temperatures and pressures. The conversion products are sought as liquid fuels, especially the $C_5^+$ aliphatic and aromatic hydrocarbons. Olefinic gasoline is produced in good yield by the MOGD process and may be recovered as a product or recycled to the reactor system for further conversion to distillate-range products. Operating details for typical MOGD units are disclosed in U.S. Pat. Nos. 4,445,031, 4,456,779 (Owen et al) and 4,433,185 (Tabak), incorporated herein by reference.

In addition to their use as shape selective oligomerization catalysts, the medium pore ZSM-5 type catalysts are useful for converting methanol and other lower aliphatic alcohols or corresponding ethers to olefins. Particular interest has been directed to a catalytic process for converting low cost methanol to valuable hydrocarbons rich in ethene and $C_3^+$ alkenes. Various processes are described in U.S. Pat. Nos. 3,894,107 (Butter et al), 3,928,483 (Chang et al), 4,025,571 (Lago), 4,423,274 (Daviduk et al) and 4,433,189 (Young), incorporated herein by reference. It is generally known that the MTO process can be optimized to produce a major fraction of $C_2$–$C_4$ olefins. Prior process proposals have included a separation section to recover ethene and other gases from byproduct water and $C_5^+$ hydrocarbon liquids. These oligomerization process conditions which favor the production of $C_{10}$–$C_{20}$ and higher aliphatics tend to convert only a small portion of ethene as compared to $C_3^+$ olefins.

SUMMARY OF THE INVENTION

It has been discovered that methanol, DME or the like may be converted to liquid fuels, particularly distillate, in a multi-stage continuous process, with integration between the major process units providing an ethene-rich recycle stream. The initial stage MTO type process hydrocarbon effluent stream, after byproduct water separation, can be fed to the MOGD stage for conversion to heavier hydrocarbons. Ethene may be recovered by interstage separation and/or unconverted ethene from the oligomerization stage may be recovered for recycle. Advantageously, the recycled ethene is found to be reactive with methanol/DME or other oxygenates in the presence of ZSM-5 type catalysts. In effect a novel MTO-MOGD system is provided wherein the ethene component may be recycled substantially to extinction.

In a preferred embodiment, the invention provides methods and apparatus for an integrated continuous technique for converting oxygenated organic feedstock to liquid hydrocarbons comprising means for (a) contacting feedstock with zeolite catalyst in a primary catalyst stage at elevated temperature and moderate pressure to convert at least a portion of the feedstock oxygenate to hydrocarbons containing a major fraction of $C_2$–$C_4$ olefins and a minor fraction containing $C_5^+$ hydrocarbons;

(b) cooling and separating effluent from step (a) to provide an aqueous liquid byproduct stream, a heavy hydrocarbon liquid stream and a light hydrocarbon vapor stream rich in $C_2$–$C_4$ olefins;

(c) compressing at least a portion of the olefinic light hydrocarbon stream to condense a liquid olefinic hydrocarbon stream rich in $C_3^+$ olefins and recovering an ethene-rich gaseous stream;

(d) further pressurizing and contacting substantially all of the condensed liquid olefinic hydrocarbon stream in a secondary catalytic stage with oligomerization catalyst comprising medium-pore shape selective acidic zeolite at substantially increased pressure and moderate temperature to convert at least a portion of olefins to a heavier liquid hydrocarbon product stream comprising olefinic gasoline and distillate range liquids; and (e) recovering ethene in a gaseous stream for recycle to the primary catalytic stage.

Advantageously, the primary and secondary stage catalyst comprises ZSM-5 type zeolite and ethene is recycled to the primary stage at a rate of about 1 to 20 parts ethene per 100 parts by weight of methanol equivalent in the feedstock. By fractionating gaseous effluent separated from the primary staged effluent a recycle gas stream may be recovered containing at least 90% of ethene from the primary catalytic stage and an olefinic stream rich in $C_3^+$ olefins.

Other objects and features of the invention will be seen in the following description and drawings.

THE DRAWINGS

DESCRIPTION OF PREFERRED EMBODIMENTS

Figure 1:
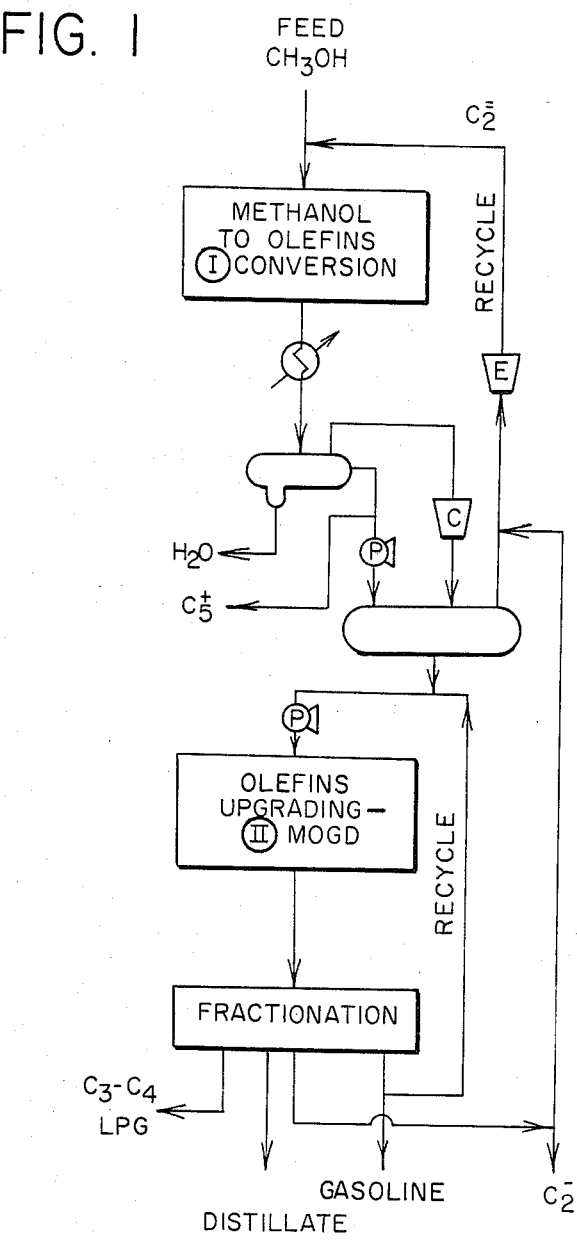
FIG. 1 is a process flow sheet showing the major unit operations and process streams.

Numerous oxygenated organic compounds may be contained in the feedstock material to be converted in the primary stage. Since methanol or its ether derivative (DME) are industrial commodities available from synthesis gas or the like, these materials are utilized in the description herein as preferred starting materials. It is understood by those skilled in the art that MTO-type processes can employ methanol, dimethylether and mixtures thereof, as well as other aliphatic alcohols, ethers, ketones and/or aldehydes. It is known in the art to partially convert oxygenates by dehydration, as in the catalytic reaction of methanol over gamma-alumina to produce DME intermediate. Typically, an equilibrium mixture ($CH_3OH \rightleftharpoons CH_3OCH_3 + H_2O$) is produced by partial dehydration. This reaction takes place in either conversion of methanol to lower olefins (MTO) or methanol to gasoline (MTG).

Catalyst versatility permits the same zeolite to be used in both the primary conversion stage (MTO) and secondary oligomerization stage (MOGD). While it is within the inventive concept to employ substantially different catalysts in these stages, it is advantageous to employ a standard ZSM-5 having a silica alumina molar ratio of 70:1.

The oligomerization catalysts preferred for use herein include the crystalline aluminosilicate zeolites having a silica to alumina ratio of at least 12, a constraint index of about 1 to 12 and acid cracking activity of about 160–200. Representative of the ZSM-5 type zeolites are ZSM-5, ZSM-11, ZSM-12, ZSM-22, ZSM-23, ZSM-35 and ZSM-38. ZSM-5 is disclosed and claims in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable catalyst for fixed bed operation is HZSM-5 zeolite with 35 wt.% alumina binder in the form of cyclindrical extrudates of about 1–5 mm. These medium pore shape selective catalysts are sometimes known as porotectosilicates or "pentasil" catalysts.

Other catalysts and processes suitable for converting methanol/DME to lower olefins are disclosed in U.S. Pat. Nos. 4,393,265 (Bonifaz), 4,387,263 (Vogt et al.) and European Patent application No. 0081683 (Marosi et al.), and ZSM-45. In addition to the preferred aluminosilicates, the borosilicate, ferrosilicate and "silicalite" materials may be employed. ZSM-5 type catalysts are particularly advantageous because the same material may be employed for dehydration of methanol to DME, conversion to lower olefins and oligomerization.

In this description, metric units and parts by weight are employed unless otherwise stated. Various reactor configurations may be used, including fluidized bed catalytic reactors, moving bed and fixed bed reactors.

Referring to FIG. 1, the process feedstock (methanol or DME, for instance) is fed to the primary stage I where it is converted to lower olefins and gasoline hydrocarbon plus water by dehydration of the oxygenated feedstock. Byproduct water is recovered by simple phase separation from the cooled effluent. Liquid hydrocarbons consisting essentially of $C_5^+$ gasoline range materials may be recovered or pumped to the higher secondary stage pressure. At least a portion of the vapor phase effluent from the primary stage is compressed and heated along with gasoline diluent or throughput liquids to oligomerization reaction temperature, and the combined olefinic stream (optionally containing recycled olefinic gasoline) is reacted at high pressure and elevated temperature over the catalyst. Secondary stage II effluent is then separated into light gases, $C_5^+$ gasoline for recycle in part and distillate range hydrocarbons. The distillate stream comprises a major fraction of $C_{10}$-$C_{20}$ high boiling aliphatics and may contain a minor amount of aromatics.

In the process for catalytic conversion of olefins to heavier hydrocarbons by catalytic oligomerization using an acid crystalline zeolite, such as ZSM-5 type catalyst, process conditions can be varied to favor the formation of either gasoline or distillate range products. At moderate temperature and relatively high pressure, the conversion conditions favor distillate range product having a normal boiling point of at least 165° C. (330° F.). Lower olefinic feedstocks containing $C_2$-$C_6$ alkenes may be converted selectively; however, the distillate mode conditions do not convert a major fraction of ethylene. While propene, butene-1 and others may be converted to the extent of 50 to 95% in the distillate mode, only about 10 to 50% of the ethylene component will be consumed.

Alkylation of ethylene with methanol over ZSM-5 catalyst has been described by Kaeding et al (J. Catalysis; January 1980, August 1984), and it is known to recycle ethene in the production of aromatic gasoline from methanol over zeolites (U.S. Pat. No. 3,998,899, Daviduk). In a fluidized bed plant for converting methanol to lower olefins and gasoline, recycle of ethylene at a rate of 2.5 parts by weight be 100 parts $CH_2$ equivalent in the feedstock methanol provides a product yield that is substantially the same, as shown in Table I. These continuous runs are conducted at the same conditions.

TABLE I

| | Hydrocarbon Product Yield, Wt % | |
|---|---|---|
| Component | Without Recycle | With ethene Recycle |
| $C_1$ | 0.8 | 0.8 |
| $C_2$ | 0.3 | 0.3 |
| $C_2=$ | 2.5 | 2.7 |
| $C_3$ | 4.4 | 4.5 |
| $C_3=$ | 4.6 | 4.5 |
| $nC_4$ | 2.1 | 2.1 |
| $iC_4$ | 10.8 | 10.4 |
| $C_4=$ | 5.4 | 5.1 |
| $C_5+$ (Gasoline) | 69.1 | 69.6 |
| Total | 100.0 | 100.0 |

T = 407° C.,
P = 400KPa,
WHSV = 2.65$^-$ hr (based on HZSM-5 catalyst).

Figure 2:
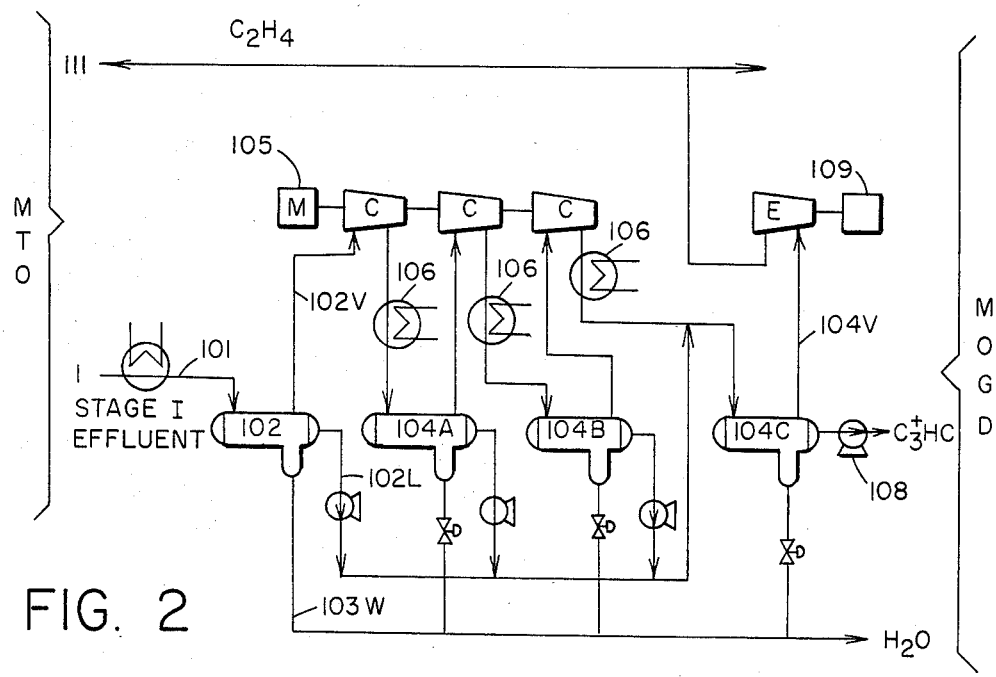
FIG. 2 is a schematic representation of a preferred inter-stage separation system for ethene recovery.

In the embodiment of FIG. 2, the light hydrocarbon vapor stream separated from the primary stage effluent is compressed in a plurality of compression stages to condense liquid olefinic hydrocarbons. The full reaction effluent of the primary stage MTO plant is passed via conduit 101 and primary phase separator 102 to provide a first vapor stream 102V, rich in C$_4$-hydrocarbons, liquid hydrocarbons stream 102L, and by product water stream 103W. The liquid (eg-C$_5$+) stream 102L is combined with a corresponding liquid HC from succeeding separators and withdrawn. The primary vapor stream 102V is adiabatically compressed by multi-stage motor-compressor set 105 M-C, cooled via exchanger 106 and passed to a succeeding separator 104A, at which point the preceeding phase separation technique is repeated. Likewise other separators 104B and 104C operate to provide an ethene-rich recycle stream 104V, which is passed to turbo-expander 109E and thus at MTO pressure back via line 111 to the olefins production in the primary stage. Advantageously, the MTO effluent is received at about atmospheric pressure (eg, 100-150 kPa) and compressed in plural stages to an intermediate pressure of about 1100-3500 kPa (150-400 psig) and separated in the final vessel 104C at about ambient temperature (20°-60° C.). Olefinic liquids rich in C$_3$+ aliphatic are recovered from the final compressor stage via pump 108 which pressurizes the liquid HC stream to sufficiently high pressure to be employed in the following secondary stage MOGD unit.

Figure 3:
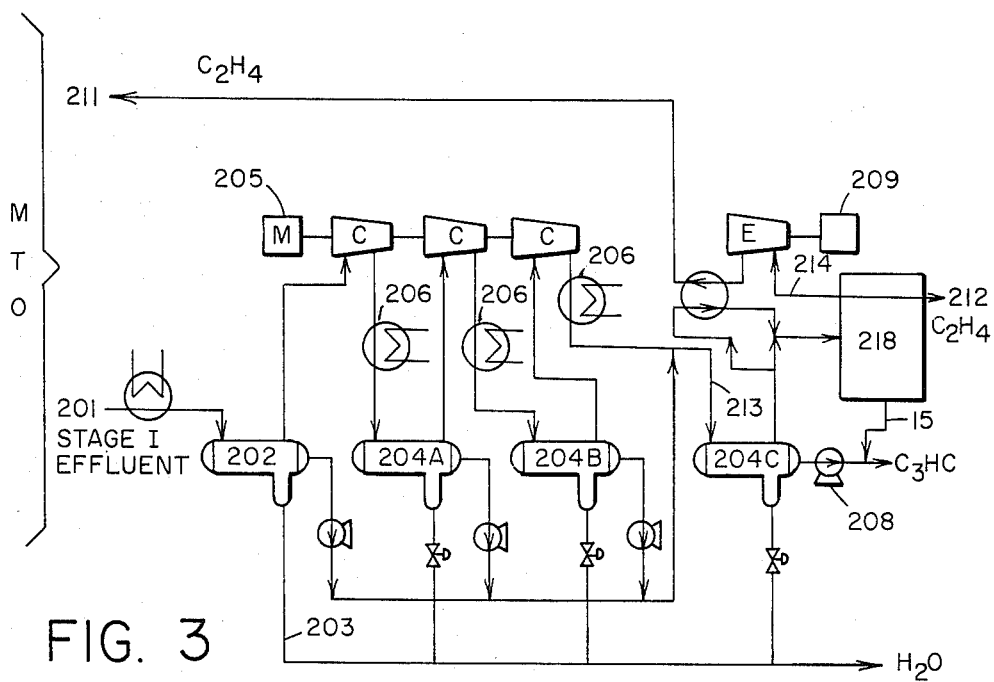
FIG. 3 is a schematic representation of an alternative system.

A further modification of the interstage ethene separation technique described above is depicted in the flow diagram in FIG. 3, wherein corresponding apparatus and process streams are identified by corresponding numbers. In this adaption, ethene-rich vapor withdrawn from the first separator 204C via line 213 is cooled by heat exchanger and further processed to increase ethene purity in ethylene unit 216. As will be understood by one skilled in the art, ethene can be treated in a cryogenic plant cold box, de-ethanizer tower, absorption unit or the like to remove undesirable components prior to recycle 211 and/or recovery 212. A suitable selective sorption unit is disclosed in U.S. Pat. No. 4,471,147 (Hsia et al), incorporated herein by reference. Preferably, compressed light hydrocarbons are fractionated to recover a recycle stream containing at least 90 mole percent ethene. This can be achieved by selectively absorbing C$_3$+ components in a C$_5$+ liquid hydrocarbon sorbent stream.

Figure 4:
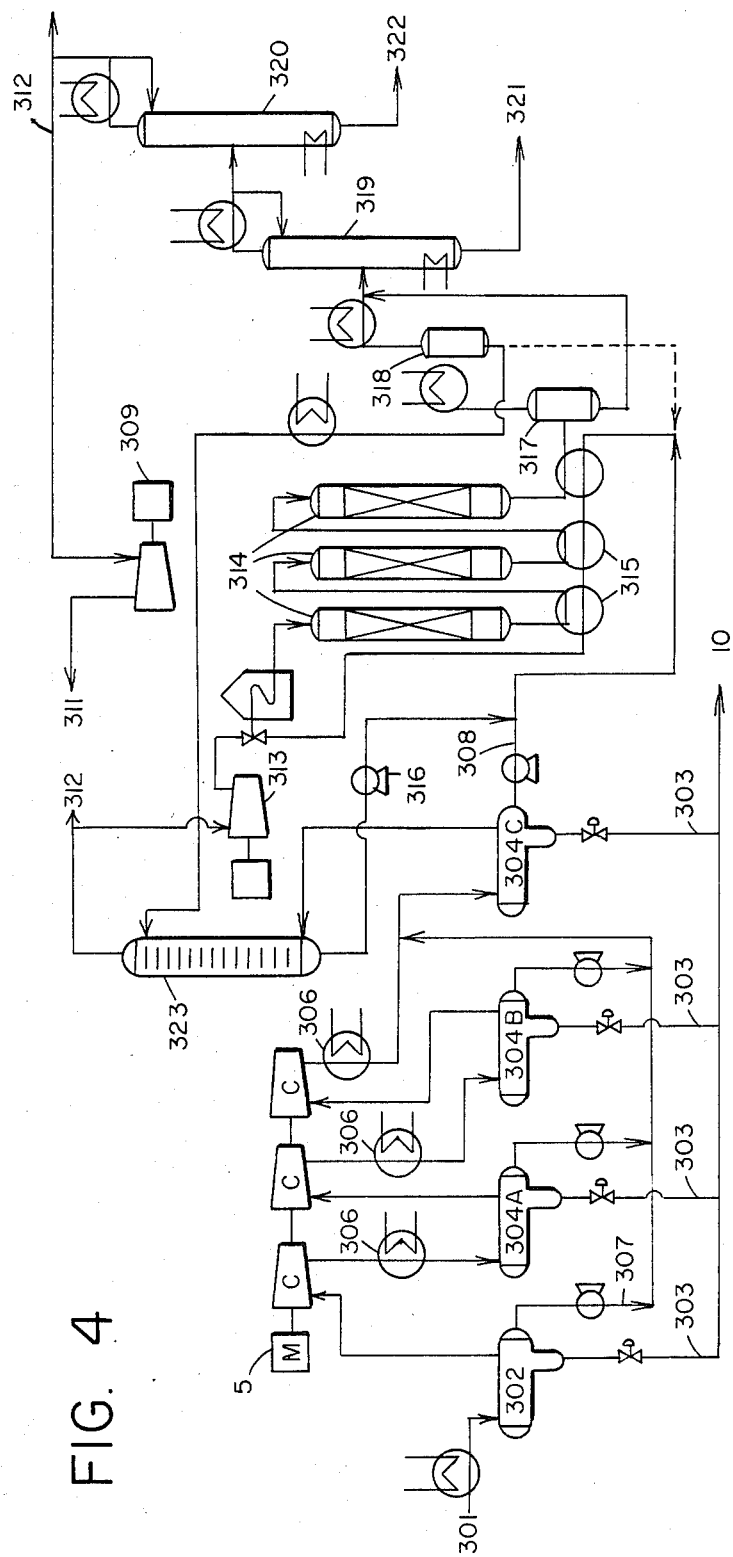
FIG. 4 is a preferred embodiment of an integrated process, depicted by process flow sheet.

In FIG. 4 a continuous multi-stage catalytic system is depicted for converting oxygenated feedstock to liquid hydrocarbons. The process flow diagram shows an integrated plant. The primary stage includes catalytic reactor means containing acidic zeolite catalyst for converting oxygenate to olefinic hydrocarbons rich in C$_2$-C$_4$ alkenes. The interstage section includes separation means for recovering water and light hydrocarbon vapor from the primary stage effluent stream, means for pressurizing the primary stage hydrocarbon effluent stream to recover an intermediate hydrocarbon liquid stream rich in C$_3$+ components and an ethene-rich vapor stream. The secondary stage includes catalytic oligomerization reactor means containing medium pore shape selective acidic zeolite oligomerization catalyst for converting the C$_3$+ olefinic hydrocarbons to heavier liquid hydrocarbons. Fractionation means 317, 318, 319, 320 provide towers for separating secondary stage effluent into a light hydrocarbon stream containing C$_2$-C$_4$ aliphatic hydrocarbons, a C$_5$+ gasoline stream and distillate range stream. By recovering and recycling at least a portion of the ethene to the primary stage for combining with oxygenated feedstock, an economic system is achieved.

The combined processes are an effective means for converting oxygenated organic compounds, such as methanol, DME, lower aliphatic ketones, aldehydes, esters, etc, to valuable hydrocarbon products. Thermal integration is achieved by employing heat exchangers between various process streams, towers, absorbers, etc.

Various modifications can be made to the system, especially in the choice of equipment and non-critical processing steps. While the invention has been described by specific examples, there is no intent to limit the inventive concept as set forth in the following claims.

We claim:

1. An integrated continuous process for converting oxygenated organic feedstock to liquid hydrocarbons comprising the steps of
   (a) contacting feedstock with zeolite catalyst in a primary catalyst stage at elevated temperature and moderate pressure to convert at least a portion of the feedstock oxygenate to hydrocarbons containing a major fraction of C$_2$-C$_4$ olefins and a minor fraction containing C$_5$+ hydrocarbons;
   (b) cooling and separating effluent from step (a) to provide an aqueous liquid byproduct stream, a heavy hydrocarbon liquid stream and a light hydrocarbon vapor stream rich in C$_2$-C$_4$ olefins;
   (c) compressing at least a portion of the olefinic light hydrocarbon stream to condense a liquid olefinic hydrocarbon stream rich in C$_3$+ olefins and recovering an ethene-rich gaseous stream;
   (d) further pressurizing and contacting substantially all of the condensed liquid olefinic hydrocarbon stream from step (c) in a secondary catalytic stage with oligomerization catalyst comprising medium-pore shape selective acidic zeolite at substantially increased pressure and moderate temperature to convert at least a portion of olefins to a heavier liquid hydrocarbon product stream comprising olefinic gasoline and distillate range liquids; and
   (e) recovering ethene in a gaseous stream for recycle to the primary catalytic stage.

2. The process of claim 1 further comprising the step of fractionating gaseous effluent from separation step (b) to recover a recycle gas stream containing at least 90% of ethene from the primary catalytic stage and an olefinic stream rich in C$_3$+ olefins.

3. The process of claim 1 wherein the primary and secondary stage catalyst comprises ZSM-5 type zeolite and ethene is recycled to the primary stage at a rate of about 1 to 20 parts ethene per 100 parts by weight of methanol equivalent in the feedstock.

4. The process of claim 1 wherein primary stage feedstock comprising methanol and/or dimethyl ether and recycled ethene are converted over HZSM-5 catalyst to provide a light olefinic hydrocarbon vapor stream comprising a major amount of C$_3$-C$_4$ olefins and a minor amount of ethene.

5. The process of claim 4 wherein olefin production is optimized by employing fluid bed primary stage conditions in the temperature range of about 425° C. to 550° C., a pressure range of about 100 to 800 kPa and weight hourly space velocity range of about 0.5 to 3.0 based on ZSM-5 equivalent catalyst and methanol equivalent in the primary stage feedstock.

6. The process of claim 5 wherein at least 90% of feedstock is converted per reactor pass and wherein water diluent is cofed with methanol and/or dimethyl ether in a molar ratio of about 0.01:1 to 2:1.

7. The process of claim 4 wherein primary stage hydrocarbon effluent contains about 1 to 10 wt.% ethene and about 10 to 60 wt.% $C_3$–$C_4$ olefins.

8. The process of claim 4 wherein ethene is recovered from the primary stage effluent vapor stream by fractionation.

9. The process of claim 1 wherein the secondary stage effluent is cooled and separated to provide a light hydrocarbon stream containing unconverted ethene and wherein said unconverted ethene is expanded to about primary stage pressure for recycle.

10. The process of claim 9 wherein compressed light hydrocarbon vapor is recompressed to recover an ethene-rich recycle stream.

11. The process of claim 1 wherein the secondary stage process conditions are maintained to produce heavy liquid hydrocarbons having a normal boiling point greater than about 175° C.

12. The process of claim 11 wherein the secondary stage employs a fixed bed of ZSM-5 type catalyst to oligomerize olefins at a temperature of about 190° C. to 315° C. and pressure of about 4200 to 7000 kPa.

13. A continuous multi-stage catalytic system for converting oxygenated feedstock to liquid hydrocarbons comprising primary stage catalytic reactor means containing acidic zeolite catalyst for converting oxygenate to olefinic hydrocarbons rich in $C_2$–$C_4$ alkenes;

interstage separation means for recovering water and light hydrocarbon vapor from the primary stage effluent stream; including means for pressurizing the primary stage hydrocarbon liquid stream rich in $C_3$+ components and an ethene-rich vapor stream;

secondary stage catalytic oligomerization reactor means containing medium pore shape selective acidic zeolite oligomerization catalyst for converting $C_3$+ olefinic hydrocarbons to heavier liquid hydrocarbons;

fractionation means for separating secondary stage effluent into a light hydrocarbon stream containing $C_2$–$C_4$ aliphatic hydrocarbons, a $C_5$+ gasoline stream and distillate range stream;

means for recovering and recycling at least a portion of the ethene to the primary stage for combining with oxygenated feedstock.

14. A process for converting feedstock consisting essentially of methanol, dimethyl ether or mixtures thereof to liquid hydrocarbons comprising the steps of contacting the feedstock with zeolite catalyst in a primary catalyst stage at elevated temperature and moderate pressure to convert feedstock to hydrocarbons comprising $C_2$–$C_4$ olefins and $C_5$+ hydrocarbons;

cooling and separating effluent from the primary stage to recover a liquid hydrocarbon stream and a light hydrocarbon vapor stream rich in $C_2$–$C_4$ olefins;

compressing the olefinic light hydrocarbon stream to condense a liquid olefinic hydrocarbon stream rich in $C_3$+ olefins and recovering an ethene-rich gaseous stream;

further pressurizing and contacting the condensed liquid olefinic hydrocarbon stream in a secondary catalytic stage with oligomerization catalyst comprising medium-pore shape selective acidic zeolite at substantially increased pressure and moderate temperature to convert at least a portion of olefins to a heavier liquid hydrocarbon product stream comprising olefinic gasoline and distillate range liquids; and recovering ethene in a gaseous stream for recycle to the primary catalytic stage.

15. The process of claim 14 wherein primary stage feedstock is converted over HZSM-5 catalyst to provide a light olefinic hydrocarbon vapor stream comprising a major amount of $C_3$–$C_4$ olefins and a minor amount of ethene.

16. The process of claim 14 further comprising the step of fractionating gaseous effluent separated from primary stage effluent to recover a recycle gas stream containing at least 90% of ethene from the primary catalytic stage and an olefinic stream rich in $C_3$+ olefins.

17. The process of claim 14 wherein the primary and secondary stage catalyst comprises ZSM-5 type zeolite and ethene is recycled to the primary stage at a rate of about 1 to 10 parts ethene per 100 parts by weight of methanol equivalent in the feedstock.

18. The process of claim 14 wherein the light hydrocarbon vapor stream separated from the primary stage effluent is compressed in a plurality of compression stages to condense liquid olefinic hydrocarbons, and wherein uncondensed compressed light hydrocarbons are further fractionated to recover a recycle stream containing at least 90 mole percent ethene.

19. The process of claim 18 wherein the compressed light hydrocarbon gaseous stream is further fractionated by selectively absorbing $C_3$+ components in a $C_5$+ liquid hydrocarbon sorbent stream.

20. The process of claim 19 wherein a fraction of the secondary stage liquid hydrocarbon product stream comprising olefinic gasoline is recycled as the sorbent stream.

* * * * *